(12) United States Patent
Kagkadis

(10) Patent No.: US 7,307,176 B2
(45) Date of Patent: Dec. 11, 2007

(54) INCLUSION COMPLEX OF TAXOL WITH 2-HYDROXYPROPYL-BETA-CYCLODEXTRIN

(75) Inventor: Konstantinos Anastasios Kagkadis, Athens (GR)

(73) Assignee: Vianex S.A., Erithrea (GR)

( * ) Notice: Subject to any disclaimer, the term of this patent is extended or adjusted under 35 U.S.C. 154(b) by 0 days.

(21) Appl. No.: 10/495,373

(22) PCT Filed: Nov. 15, 2002

(86) PCT No.: PCT/IB02/05058

§ 371 (c)(1),
(2), (4) Date: Sep. 20, 2004

(87) PCT Pub. No.: WO03/043662

PCT Pub. Date: May 30, 2003

(65) Prior Publication Data

US 2005/0009783 A1    Jan. 13, 2005

(30) Foreign Application Priority Data

Nov. 19, 2001 (GB) ................................. 0127677.3

(51) Int. Cl.
C07D 305/00 (2006.01)
C08B 37/16 (2006.01)
(52) U.S. Cl. ........................ 549/510; 549/511; 536/103
(58) Field of Classification Search ................ 549/510, 549/511; 536/103
See application file for complete search history.

(56) References Cited

U.S. PATENT DOCUMENTS 5,684,169 A * 11/1997 Hamada et al. ............. 549/510
6,284,746 B1 * 9/2001 Szente et al. ................ 514/58
6,284,747 B1 9/2001 Rubinfeld .................... 514/58

FOREIGN PATENT DOCUMENTS

EP    0 639 380 A1    2/1995

OTHER PUBLICATIONS

Dordunoo et al, Solubililty and Stability of taxol : effects of buffers and cyclodextrins, 1996, International Journal of Pharmaceutics, 133, (1,2), p. 191-201.*
Sharma et al.; "Pharmaceutical and Physical Properties of Paclitaxel (Taxol) Complexes with Cyclodextrins"; 1088 Journal of Pharmaceutical Sciences, vol. 84, No. 10, Oct. 1995; pp. 12231230.
Zhang et al.; "A Review of Recent Applications of Cyclodextrins for Drug Discovery"; Exp. Opin. Ther. Patents (1999) 9 (12).
Szente et al.; "Highly Soluble Cyclodextrin Derivatives: Chemistry, Properties, and Tends in Development"; Advanced Drug Delivery Reviews 36 (1999) 17-28.
Backensfeld et al.; "Effect of Cyclodextrin Derivatives on Indomethacin Stability in Aqueous Solution"; *Pharmaceutical Research*, vol. 7, No. 5, 1990, pp. 484-490.

* cited by examiner

*Primary Examiner*—Taylor Victor Oh
(74) *Attorney, Agent, or Firm*—Renner, Otto, Boisselle & Sklar, LLP

(57) ABSTRACT

The present invention relates to a method for producing a 2-hydroxypropyl-beta-cyclodextrin inclusion complex of taxol, said 2-hydroxypropyl-beta-cyclodextrin having a degree of substitution of 0.4 to about 0.9, wherein the method comprises admixing the 2-hydroxypropyl-beta-cyclodextrin with taxol at a molar ratio of 1-1000 times with respect to taxol. A second aspect of the invention relates to a method for improving the solubility of taxol, said method comprising: (i) dissolving taxol in ethanol; (ii) dissolving 2-hydroxypropyl-beta-cyclodextrin, having a degree of substitution of 0.4 to about 0.9, in water; (iii) admixing the solution from step (i) with the solution from step (ii) and stirring, shaking or heating. A third aspect of the invention provides a 2-hydroxypropyl-beta-cyclodextrin inclusion complex of taxol, wherein said 2-hydroxypropyl-beta-cyclodextrine has a degree of substitution of 0.4 to about 0.9.

24 Claims, No Drawings

INCLUSION COMPLEX OF TAXOL WITH 2-HYDROXYPROPYL-BETA-CYCLODEXTRIN

The present invention relates to novel inclusion complexes of taxol which exhibit improved solubility properties. More specifically, the invention provides a method for solubilising taxol which comprises forming a cyclodextrin inclusion complex.

Taxol is a substance that is capable of inhibiting the division of cancer cells and which originates from the bark of a species of North American yew tree (*Taxus brevifolia*). Over recent years, taxol has emerged as a powerful anti-cancer agent which is known to be particularly effective in the treatment of ovarian cancer. However, due to its poor solubility in water, the use of taxol in medicine has been severely limited as it has proved extremely difficult to administer pharmacologically active doses to patients.

The present invention seeks to alleviate the problems associated with taxol administration by providing a novel formulation that exhibits improved solubility properties in water. In particular, the present invention seeks to provide a method for producing a taxol formulation with improved solubility properties in a convenient and economically advantageous manner which reduces the need for organic solvents.

Other objects of the invention will become apparent from the following description.

A first aspect of the invention provides a method for producing a 2-hydroxypropyl-beta-cyclodextrin inclusion complex of taxol, said 2-hydroxypropyl-beta-cyclodextrin having a degree of substitution of about 0.4 to about 0.9, wherein the method comprises admixing the 2-hydroxypropyl-beta-cyclodextrin with taxol at a molar ratio of 1-1000 times with respect to taxol.

Preferably the molar ratio of 2-hydroxypropyl-beta-cyclodextrin to taxol is 1-500:1, more preferably 1-100:1, 1-50:1 or 1-25:1.

As used herein, the term "2-hydroxypropyl-beta-cyclodextrin" refers to a compound consisting of a ring of 7 D-glucose units linked by alpha-1,4 glycosidic bonds, wherein a certain proportion of the hydroxyl groups are substituted with a 2-hydroxypropyl functional group through an ether bond.

By way of definition, the term "degree of subsitution" refers to the average number of hydroxyl groups per cyclodextrin molecule that are substituted by a hydroxypropyl group. For example, a degree of substitution of about 0.4 to about 0.9 means that an average of 0.4 to 0.9 hydroxyl groups per cyclodextrin are substituted by a hydroxypropyl group.

The method of the present invention results in the formation of a 2-hydroxypropyl-beta-cyclodextrin inclusion complex (or clathrate) of taxol which has a markedly improved solubility in water. Consequently, this improved solubility serves to make taxol more easily absorbed when administered to cancer patients and allows the physiological effects of taxol to be more effectively induced.

Preferably, the reaction takes place in an aqueous system, or in an organic solvent-water system.

Even more preferably the reaction takes place in an ethanol-water mixture.

In a particularly preferred embodiment, the taxol is dissolved in ethanol and the 2-hydroxypropyl-beta-cyclodextrin is dissolved in water. The amount of the ethanol is not limited in any way as long as it is sufficient to dissolve the taxol. Likewise, the amount of water is not limited in any way, as long as it is sufficient to dissolve the 2-hydroxypropyl-beta-cyclodextrin.

A second aspect of the invention provides a method for improving the solubility of taxol, said method comprising:
(i) dissolving taxol in ethanol;
(ii) dissolving 2-hydroxypropyl-beta-cyclodextrin having a degree of substitution of about 0.4 to about 0.9 in water;
(iii) admixing the solution from step (i) with the solution from step (ii) and stirring, shaking or heating.

Preferably, the stirring or shaking is conducted as vigorously as possible for a period of from a few minutes to several tens of minutes. Stirring is generally preferred for complete mixing of the solution, and more preferably, a mechanical or magnetic stirrer, or the like, is used for vigorous stirring.

The following preferred features apply to both the first and second aspects of the invention.

In one preferred embodiment, the method comprises adding the 2-hydroxypropyl-beta-cyclodextrin in water to the ethanolic taxol solution, preferably while (or followed by) stirring or shaking.

In an alternative preferred embodiment, the method comprises adding the ethanolic taxol solution to the 2-hydroxypropyl-beta-cyclodextrin in water, preferably while (or followed by) stirring or shaking.

In another preferred embodiment, the molar ratio of 2-hydroxypropyl-beta-cyclodextrin to taxol is 1-1000:1, preferably 1-500:1, more preferably 1-100:1, 1-50:1 or 1-25:1.

More preferably, the molar ratio of 2-hydroxypropyl-beta-cyclodextrin to taxol is 10:1.

Even more preferably, the molar ratio of 2-hydroxypropyl-beta-cyclodextrin to taxol is 5:1.

More preferably still, the molar ratio of 2-hydroxypropyl-beta-cyclodextrin to taxol is 1:1.

Experiments have indicated that if the ratio of 2-hydroxypropyl-beta-cyclodextrin to taxol is less than the lower limit of 1:1, the solubility of taxol is not significantly increased, whereas if it is greater than 1000:1, the excessive amount of 2-hydroxypropyl-beta-cyclodextrin discourages inclusion complex formation.

It is notable that when taxol is admixed with 2-hydroxypropyl-beta-cyclodextrin at a high ratio, part of the taxol may remain undissolved. In such a case, the undissolved compound can be removed from the reaction mixture by means of filtration.

In a preferred embodiment, the reaction time is from 1 minute to 48 hours.

In another preferred embodiment, the 2-hydroxypropyl-beta-cyclodextrin is present in a concentration of 0.0001 to 200% by weight, based on the weight of water.

Even more preferably, the 2-hydroxypropyl-beta-cyclodextrin is present in a concentration of 1 to 50% by weight, based on the weight of water.

In another preferred embodiment, the 2-hydroxypropyl-beta-cyclodextrin is present in a concentration of 1 to 100,000,000 times the mole amount of the taxol.

More preferably, the 2-hydroxypropyl-beta-cyclodextrin is present in an amount of 100 to 100,000 times the mole amount of the taxol.

In one particularly preferred embodiment, the taxol is dissolved in ethanol, whilst the 2-hydroxypropyl-beta-cyclodextrin is dissolved in water to form an aqueous solution containing the 2-hydroxypropyl-beta-cyclodextrin in an amount of 1 to 100,000,000 times, preferably 100 to 100,000 times the mole amount of the taxol. The 2-hydroxypropyl-beta-cyclodextrin solution is then added to the taxol solution. Alternatively, the 2-hydroxypropyl-beta-cyclodextrin may be added directly to a taxol solution. Upon the addition, the taxol solution is stirred, preferably in a vigorous manner using a stirrer or the like.

In a preferred embodiment, the reaction is carried out at a temperature of about 15° to about 90° C. There is no particular restriction on the temperature at which the inclusion reaction is carried out, and the reaction proceeds to a sufficient degree at room temperature. The reaction time typically ranges from a few minutes to several hours.

In a particularly preferred embodiment, the reaction is carried out at a temperature of about 15° to about 40° C.

A third aspect of the invention relates to a 2-hydroxypropyl-beta-cyclodextrin inclusion complex of taxol, wherein said 2-hydroxypropyl-beta-cyclodextrin has a degree of substitution of about 0.4 to about 0.9.

The inclusion products of taxol according to the invention have a markedly improved solubility in aqueous phase and hence can be delivered in a more effective manner to diseased body parts of patients suffering from cancer.

In one particularly preferred embodiment of the invention, the aqueous solution of the 2-hydroxypropyl-beta-cyclodextrin inclusion product of taxol can be dried to form a powder. In this way, a stable 2-hydroxypropyl-beta-cyclodextrin inclusion complex of taxol may be obtained, which is highly soluble in water.

The 2-hydroxypropyl-beta-cyclodextrin inclusion complex of taxol in accordance with the invention may be used in a variety of different forms. For example, it may be prepared as an injectable drug or used as a powder without further processing, or the powder may be granulated, tableted or filled into capsules. The inclusion product of the invention may also be used in the form of the original solution.

Pharmaceutical Compositions

In one preferred embodiment, the taxol inclusion complex of the invention is admixed with a pharmaceutically acceptable diluent, carrier or excipient, (including combinations thereof) to form a pharmaceutical composition.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable carriers include lactose, starch, glucose, methyl cellulose, magnesium stearate, mannitol, sorbitol and the like. Examples of suitable diluents include ethanol, glycerol and water.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different formulation requirements dependent on the different delivery systems. By way of example, the complex of the present invention may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a combination of routes.

Administration

The 2-hydroxypropyl-beta-cyclodextrin inclusion complex of taxol obtained in accordance with the above described methods may be administered to a patient intravenously, orally or via another route. By such administration, a minute, but highly efficient dosage taxol may be delivered to the patient.

The 2-hydroxypropyl-beta-cyclodextrin inclusion complex of taxol may be administered alone but will generally be administered as a pharmaceutical composition e.g. when the complex is in admixture with a suitable pharmaceutical excipient, diluent or carrier selected with regard to the intended route of administration and standard pharmaceutical practice.

For example, the complex can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

If the complex is in the form of a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropyl-methylcellulose (HPMC), hydroxypropyl-cellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compound may be combined with various sweetening or flavouring agents, colouring matter or dyes, with emulsifying and/or suspending agents and with diluents such as water, ethanol, propylene glycol and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracere-broventricular, intracerebral, subcutaneous, ophthalmic (including intravitreal or intracameral), transdermal, rectal, buccal, vaginal, epidural, sublingual.

If the complex of the invention is administered parenterally, then examples of such administration include one or more of: intravenously, intra-arterially, intraperitoneally, intrathecally, intraventricularly, intraurethrally, intrasternally, intracranially, intramuscularly or subcutaneously administering the component; and/or by using infusion techniques.

For parenteral administration, the complex may be in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For buccal or sublingual administration the complex may be administered in the form of tablets or lozenges which can be formulated in a conventional manner.

As indicated, the complex of the invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the agent and a suitable powder base such as lactose or starch.

Alternatively, the complex of the present invention can be administered in the form of a suppository or pessary, or it may be applied topically in the form of a gel, hydrogel, lotion, solution, cream, ointment or dusting powder. The complex of the present invention may also be dermally or transdermally administered, for example, by the use of a skin patch. The complex may also be administered by pulmonary, rectal or ocular routes. For ophthalmic use, the complex can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, the complex may be formulated in an ointment such as petrolatum.

For application topically to the skin, the complex of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Dose Levels

Typically, a physician will determine the actual dosage which will be most suitable for an individual subject. The specific dose level and frequency of dosage for any particular patient may be varied and will depend upon a variety of factors including the activity of the specific complex employed, the metabolic stability and length of action of that complex, the age, body weight, general health, sex, diet, mode and time of administration, rate of excretion, drug combination, the severity of the particular condition, and the individual undergoing therapy.

Depending upon the need, the complex may be administered at a dose of from 0.01 to 30 mg/kg body weight, such as from 0.1 to 10 mg/kg, more preferably from 0.1 to 1 mg/kg body weight.

The present invention will now be described by reference to the following non-limiting examples.

EXAMPLES

Preparation of the Cyclodextrin-Paclitaxel Solution

Preparation of Solution A (0.35M 2-hydroxy-propyl-beta-cyclodextrin)

45.5 g of 2-hydroxy-propyl-beta-cyclodextrin (DS 0.61) were dissolved in 50 ml water and then further diluted to 100 ml with water.

Preparation of Solution B (paclitaxel)

Paclitaxel (30 mg) was dissolved in 1 ml of absolute ethanol and stirred until a clear solution was obtained.

Preparation of Complex Solution

Very quickly and shaking vigorously, solution A was mixed with solution B to give a clear solution without any cloudiness. The solution was further diluted to 200 ml with water. The solution was placed in a 600 ml vial suitable for freeze-drying with an igloo type rubber stopper and put in the freeze-dryer.

Freeze Drying Process

The shelves were cooled from ambient temperature at a rate of −20° C./hour to −40° C. When the product temperature reached at least −35° C., it was maintained at that temperature for 1 hour. The condenser was then cooled to at least −60° C. The vacuum pump was started and the pressure reduced to 0.1 mbar or less. The shelves were then heated at a rate of +20° C./hour until temperature was +20° C. The pressure was maintained at 0.25 mbar using nitrogen microbleed and the product temperature was allowed to reach at least 15° C. The shelves were heated at a rate of 20° C./hour until the temperature was +40° C. The product temperature was allowed to reach at least 35° C. and was maintained for 8 more hours. The vacuum was then broken by nitrogen up to pressure of 0.8 bar. The rubber stopper was closed and the vial was crimped.

Product Specifications:

Water content less than 1%.

Reconstitution time using 200 ml of water: less than 60 sec.

Paclitaxel assay: 30 mg/vial.

Shelf life (stability) of the product: more than 2 years.

Various modifications and variations of the described methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The invention claimed is:

1. A method for producing a 2-hydroxypropyl-beta-cyclodextrin inclusion complex of taxol, said 2-hydroxypropyl-beta-cyclodextrin having a degree of substitution of about 0.4 to about 0.61, wherein the method comprises admixing the 2-hydroxypropyl-beta-cyclodextrin with taxol at a molar ratio of 1-1000 times with respect to taxol.

2. A method according to claim 1 which is conducted in an aqueous system, or an organic solvent-water system.

3. A method according to claim 1 which is conducted in an ethanol-water mixture.

4. A method according to claim 3 wherein the taxol is dissolved in ethanol and the 2-hydroxypropyl-beta-cyclodextrin is dissolved in water, the molar ratio of 2-hydroxypropyl-beta-cyclodextrin is 1-1000:1 and the 2-hydroxypropyl-beta-cyclodextrin is present in a concentration of 0.0001 to 200% by weight, based on the weight of water.

5. A method for improving the solubility of taxol, said method comprising:
   (i) dissolving taxol in ethanol;
   (ii) dissolving 2-hydroxypropyl-beta-cyclodextrin, having a degree of substitution of about 0.4 to about 0.61, in water;
   (iii) admixing the solution from step (i) with the solution from step (ii) and stirring, shaking and/or heating.

6. A method according to claim 4 comprising adding the 2-hydroxypropyl-beta-cyclodextrin in water to the ethanolic taxol solution.

7. A method according to claim 4 comprising adding the ethanolic taxol solution to the 2-hydroxypropyl-beta-cyclodextrin in water.

8. A method according to claim 1 wherein the molar ratio of 2-hydroxypropyl-beta-cyclodextrin to taxol is 1-1000:1.

9. The method of claim 1 wherein the molar ratio is 10:1.

10. The method of claim 1 wherein the molar ratio is 5:1.

11. The method of claim 1 wherein the molar ratio is 1:1.

12. The method of claim 1 wherein the reaction time is from 1 minute to 48 hours.

13. The method of claim 1 wherein the 2-hydroxypropyl-beta-cyclodextrin is present in a concentration of 0.0001 to 200% by weight, based on the weight of water.

14. The method of claim 1 wherein the 2-hydroxypropyl-beta-cyclodextrin is present in a concentration of 1 to 50% by weight, based on the weight of water.

15. The method of claim 1 wherein the 2-hydroxypropyl-beta-cyclodextrin is present in a concentration of 1 to 100,000,000 times the mole amount of the taxol.

16. The method of claim 1 wherein the 2-hydroxypropyl-beta-cyclodextrin is present in an amount of 100 to 100,000 times the mole amount of the taxol.

17. The method of claim 1 wherein the reaction is carried out at a temperature of about 15 to 90° C.

18. The method of claim 1 wherein the reaction is carried out at a temperature of about 15 to 40° C.

19. A 2-hydroxypropyl-beta-cyclodextrin inclusion complex of taxol, wherein said 2-hydroxypropyl-beta-cyclodextrin has a degree of substitution of about 0.4 to about 0.61.

20. The method of claim 1 which further comprises the step of freeze drying the 2-hydroxypropyl-beta-cyclodextrin inclusion complex of taxol to form a dry powder.

21. The method of claim 20 wherein the dry powder is reconstituted by dissolving in water.

22. A method for producing a 2-hydroxypropyl-beta-cyclodextrin inclusion complex of taxol, said 2-hydroxypropyl-beta-cyclodextrin having a degree of substitution of about 0.61, wherein the method comprises ad mixing the 2-hydroxypropyl-beta-cyclodextrin with taxol at a molar ratio of 1-1000 times with respect to taxol.

23. A method for improving the solubility of taxol, said method comprising:
   (i) dissolving taxol in ethanol;
   (ii) dissolving 2-hydroxypropyl-beta-cyclodextrin, having a degree of substitution of about 0.61, in water;
   (iii) admixing the solution from step (i) with the solution from step (ii) and stirring, shaking and/or heating.

24. A 2-hydroxypropyl-beta-cyclodextrin inclusion complex of taxol, wherein said 2-hydroxypropyl-beta-cyclodextrin has a degree of substitution of about 0.61.

* * * * *